US012465698B2

(12) United States Patent
Pic et al.

(10) Patent No.: US 12,465,698 B2
(45) Date of Patent: Nov. 11, 2025

(54) DEVICES AND METHODS FOR DELIVERING POWDERED AGENTS

(71) Applicant: Boston Scientific Scimed, Inc., Maple Grove, MN (US)

(72) Inventors: Andrew Pic, Northboro, MA (US); Laurie Lehtinen, Boylston, MA (US); Collin Murray, Bolton, MA (US); Nicholas Seagrave, Dudley, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 219 days.

(21) Appl. No.: 17/139,079

(22) Filed: Dec. 31, 2020

(65) Prior Publication Data

US 2021/0205543 A1 Jul. 8, 2021

Related U.S. Application Data

(60) Provisional application No. 62/957,519, filed on Jan. 6, 2020.

(51) Int. Cl.

*A61M 5/315* (2006.01)
*A61M 5/19* (2006.01)
*A61M 5/31* (2006.01)

(52) U.S. Cl.

CPC .......... *A61M 5/31596* (2013.01); *A61M 5/19* (2013.01); *A61M 5/3129* (2013.01); *A61M 2202/064* (2013.01)

(58) Field of Classification Search

CPC .............. A61M 5/19; A61M 2202/064; A61M 5/31596; A61M 37/0069; A61M 5/3015;

(Continued)

(56) References Cited

U.S. PATENT DOCUMENTS 471,854 A 3/1892 Howard
881,238 A 3/1908 Hasbrouck (Continued)

FOREIGN PATENT DOCUMENTS

CN 101401956 B 11/2012
CN 108289789 A 7/2018

(Continued)

OTHER PUBLICATIONS

Bridevaux, Pierre-Olivier, et al. "Short-term safety of thoracoscopic talc pleurodesis for recurrent primary spontaneous pneumothorax: a prospective European multicentre study." European Respiratory Journal 38.4 (2011): 770-773.

(Continued)

*Primary Examiner* — James D Ponton
*Assistant Examiner* — Hong-Van N Trinh
(74) *Attorney, Agent, or Firm* — Bookoff McAndrews, PLLC

(57) ABSTRACT

A device for delivering an agent may comprise a chamber for receiving agent through an agent inlet; and a body received within the chamber. The body may be movable in first and second directions along a longitudinal axis of the chamber. In a first configuration of the body, an amount of the agent may flow into the chamber via the agent inlet. In a second configuration of the body, the agent is prevented from flowing into the chamber via the agent inlet. When the body is transitioned from the first configuration to the second configuration, the amount of the agent may be moved from a first position along the longitudinal axis of the chamber to a second position along the longitudinal axis of the chamber.

20 Claims, 10 Drawing Sheets

(58) Field of Classification Search
CPC ...... A61M 13/003; A61M 11/007; A61J 1/20; A61J 1/2003; A61J 1/2048; A61J 1/2051; A61J 1/2055; A61J 1/2058; A61J 1/2062; A61J 1/2065; A61J 1/2089; A61J 1/2093; A61J 1/2096; A61J 1/22
See application file for complete search history.

(56) References Cited

U.S. PATENT DOCUMENTS 1,145,520 A 7/1915 Smith
1,599,959 A 9/1926 Buheiji
1,732,566 A 10/1929 McKendrick
2,151,418 A 3/1939 Bolté
2,185,927 A 1/1940 Shelanski
2,478,715 A 8/1949 Schmitt
2,623,519 A 12/1952 Cohen
3,402,712 A * 9/1968 Eisenhand ........ A61M 37/0069 604/61
3,602,398 A * 8/1971 Pollak .................. A61C 17/032 222/529
3,669,113 A 6/1972 Altounyan et al.
3,797,709 A 3/1974 Ivanovich
3,940,061 A 2/1976 Gimple et al.
4,184,258 A 1/1980 Barrington et al.
4,427,450 A 1/1984 Kostansek
4,457,329 A 7/1984 Werley et al.
4,673,395 A 6/1987 Phillips
4,806,167 A 2/1989 Raythatha
5,215,221 A 6/1993 Dirksing
5,231,983 A 8/1993 Matson et al.
5,273,531 A 12/1993 Knopfler
5,312,331 A 5/1994 Kneopfler
5,312,333 A 5/1994 Churinetz et al.
5,366,122 A 11/1994 Guentert et al.
5,376,079 A 12/1994 Holm
5,445,612 A 8/1995 Terakura et al.
5,470,311 A 11/1995 Setterstrom et al.
5,884,621 A 3/1999 Matsugi et al.
5,951,531 A 9/1999 Ferdman et al.
6,003,512 A 12/1999 Gerde
6,484,750 B1 11/2002 Foos et al.
6,554,022 B2 4/2003 Wakeman
6,589,087 B2 7/2003 Mackal et al.
6,684,917 B2 2/2004 Zhu et al.
6,708,712 B2 3/2004 Wakeman
6,716,190 B1 4/2004 Glines et al.
6,799,571 B1 10/2004 Hughes et al.
7,178,547 B2 2/2007 Mackal
7,311,270 B2 12/2007 Kapila
7,334,598 B1 2/2008 Hollars
7,361,300 B2 4/2008 Kelly et al.
7,427,607 B2 9/2008 Suzuki
7,455,248 B2 11/2008 Kablik et al.
7,461,649 B2 12/2008 Gamard et al.
7,544,177 B2 6/2009 Gertner
7,563,299 B2 7/2009 Baptista da Costa et al.
7,673,647 B2 3/2010 Mackal
7,841,338 B2 11/2010 Dunne et al.
7,892,205 B2 2/2011 Palasis et al.
7,921,874 B2 4/2011 Tekulve et al.
8,037,880 B2 10/2011 Zhu et al.
8,097,071 B2 1/2012 Burgess et al.
8,118,777 B2 2/2012 Ducharme et al.
8,269,058 B2 9/2012 McCarthy et al.
8,313,474 B2 11/2012 Campbell et al.
8,360,276 B2 1/2013 Rogier et al.
8,361,054 B2 1/2013 Ducharme et al.
8,496,189 B2 7/2013 Lomond et al.
8,673,065 B2 3/2014 Burgess et al.
8,721,582 B2 5/2014 Ji
8,728,032 B2 5/2014 Ducharme et al.
8,741,335 B2 6/2014 McCarthy
8,827,980 B2 9/2014 Ji
8,910,627 B2 12/2014 Iwatschenko et al.
8,951,565 B2 2/2015 McCarthy
9,028,437 B2 5/2015 Ott et al.
9,089,658 B2 7/2015 Dunne et al.
9,101,744 B2 8/2015 Ducharme
9,107,668 B2 8/2015 Melsheimer et al.
9,132,206 B2 9/2015 McCarthy
9,204,957 B2 12/2015 Gregory et al.
9,205,170 B2 12/2015 Lucchesi et al.
9,205,207 B2 12/2015 Ji
9,205,240 B2 12/2015 Greenhalgh et al.
9,308,584 B2 4/2016 Burgess et al.
9,310,812 B2 4/2016 Costle et al.
9,375,533 B2 6/2016 Ducharme et al.
9,492,646 B2 11/2016 Hoogenakker et al.
9,517,976 B2 12/2016 Mackal
9,545,490 B2 1/2017 Iwatschenko et al.
9,555,185 B2 1/2017 Foster et al.
9,629,966 B2 4/2017 Ji
9,636,470 B2 5/2017 Pohlmann et al.
9,707,359 B2 7/2017 Kubo
9,713,682 B2 7/2017 Eistetter et al.
9,717,897 B2 8/2017 Rogier
9,821,084 B2 11/2017 Diegelmann et al.
9,839,772 B2 12/2017 Ducharme
9,839,774 B2 12/2017 Bonaldo
9,846,439 B2 12/2017 Carman et al.
9,867,931 B2 1/2018 Gittard
9,976,660 B2 5/2018 Stanton et al.
10,004,690 B2 6/2018 Lee et al.
10,010,705 B2 7/2018 Greenhalgh et al.
10,017,231 B2 7/2018 Fawcett, Jr.
10,036,617 B2 7/2018 Mackal
10,065,004 B2 9/2018 Eder et al.
10,173,019 B2 1/2019 Kaufmann et al.
10,384,049 B2 8/2019 Stanton et al.
10,463,811 B2 11/2019 Lee et al.
10,507,293 B2 12/2019 Goodman et al.
10,646,706 B2 5/2020 Rogier
10,730,595 B2 8/2020 Fawcett
10,751,523 B2 8/2020 Rogier
10,806,853 B2 10/2020 Gittard
10,850,814 B2 12/2020 Fawcett
10,994,818 B2 5/2021 Hernandez
2004/0107963 A1 6/2004 Finlay et al.
2004/0249359 A1 12/2004 Palasis et al.
2005/0121025 A1 6/2005 Gamard et al.
2005/0147656 A1 7/2005 McCarthy et al.
2005/0220721 A1 10/2005 Kablik et al.
2006/0004314 A1 1/2006 McCarthy et al.
2006/0213514 A1 9/2006 Price et al.
2007/0056586 A1 3/2007 Price et al.
2007/0066920 A1 3/2007 Hopman et al.
2007/0066924 A1 3/2007 Hopman et al.
2007/0082023 A1 4/2007 Hopman et al.
2007/0083137 A1 4/2007 Hopman et al.
2007/0125375 A1 6/2007 Finlay et al.
2007/0151560 A1 7/2007 Price et al.
2007/0199824 A1 8/2007 Hoerr et al.
2007/0213660 A1 9/2007 Richards et al.
2008/0021374 A1 1/2008 Kawata
2008/0287907 A1 11/2008 Gregory et al.
2009/0101144 A1 4/2009 Gamard et al.
2009/0155342 A1 6/2009 Diegemann et al.
2009/0281486 A1 11/2009 Ducharme
2010/0121261 A1 5/2010 Kablik et al.
2010/0305505 A1 12/2010 Ducharme et al.
2011/0073200 A1 3/2011 Overvaag et al.
2011/0274726 A1 11/2011 Guo et al.
2011/0308516 A1 12/2011 Price et al.
2014/0271491 A1 9/2014 Gittard et al.
2015/0017601 A1* 1/2015 Fish ...................... A61C 3/025 433/88
2015/0094649 A1 4/2015 Gittard
2015/0125513 A1 5/2015 McCarthy
2016/0375202 A1 12/2016 Goodman et al.
2017/0106181 A1 4/2017 Bonaldo et al.
2017/0232141 A1 8/2017 Surti et al.
2017/0252479 A1 9/2017 Ji et al.
2017/0296760 A1 10/2017 Lee et al.
2018/0099088 A1 4/2018 Gittard

(56) References Cited

U.S. PATENT DOCUMENTS

| | | | |
|---|---|---|---|
| 2018/0193574 A1 | 7/2018 | Smith et al. |
| 2018/0214160 A1 | 8/2018 | Hoskins et al. |
| 2018/0339144 A1 | 11/2018 | Greenhalgh et al. |
| 2019/0134366 A1 | 5/2019 | Erez et al. |
| 2019/0217315 A1 | 7/2019 | Maguire et al. |
| 2019/0232030 A1 | 8/2019 | Pic et al. |
| 2021/0024187 A1 | 1/2021 | Fawcett et al. |
| 2021/0069485 A1 | 3/2021 | Rogier |

FOREIGN PATENT DOCUMENTS

| | | |
|---|---|---|
| CN | 108472666 A | 8/2018 |
| DE | 60215438 T2 | 8/2007 |
| EP | 3052168 B1 | 11/2019 |
| EP | 4275727 A2 | 11/2023 |
| JP | H07118305 A | 5/1995 |
| WO | 03013552 A1 | 2/2003 |
| WO | 2004066806 A2 | 8/2004 |
| WO | 2005062896 A2 | 7/2005 |
| WO | 2006071649 A2 | 7/2006 |
| WO | 2006088912 A2 | 8/2006 |
| WO | 2008033462 A2 | 3/2008 |
| WO | 2009061409 A1 | 5/2009 |
| WO | 2015050814 A1 | 4/2015 |
| WO | 2018157772 A1 | 9/2018 |

OTHER PUBLICATIONS

Giday, Samuel, et al. "Safety analysis of a hemostatic powder in a porcine model of acute severe gastric bleeding." Digestive diseases and sciences 58.12 (2013): 3422-3428.

Giday, Samuel A., et al. "A long-term randomized controlled trial of a novel nanopowder hemostatic agent for control of severe upper gastrointestinal bleeding in a porcine model." Gastrointestinal Endoscopy 69.5 (2009): AB133.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299.

Regalia, Kristen, et al. "Hemospray in Gastrointestinal Bleeding." Practical Gastroenterology. Endoscopy: Opening New Eyes, ser. 8, May 2014, pp. 13-24. 8.

Cook Medical. Hemospray Endoscopic Hemostat, Cook, 2014. (7 pages, in English).

"Hemospray Clinical Experience Shows Efficacy of a New Hemostasis Modality—v1", Cook Medical, 2012.

"Hemospray Clinical Experience Shows Efficacy of a New Hemostasis Modality—v2", Cook Medical, 2013.

"Hemospray Clinical Experience Shows Efficacy of a New Hemostasis Modality—v3", Cook Medical, 2014.

Aslanian, Harry R., and Loren Laine. "Hemostatic powder spray for GI bleeding." Gastrointestinal endoscopy 77.3 (2013): 508-510.

Giday, S. A., et al. "Long-term randomized controlled trial of a novel nanopowder hemostatic agent (TC-325) for control of severe arterial upper gastrointestinal bleeding in a porcine model." Endoscopy 43.04 (2011): 296-299. via ResearchGate.

RETSCH GmbH Haan. Sieve Analysis: Taking a Close Look at Quality, An Expert Guide to Particle Size Analysis. 2015. (56 pages, in English).

Micromeritics. Density Analysis, 2001. (6 pages, in English).

Micromeritics. "Application Note: Bulk and Skeletal Density Computations for the AutoPore." May 2012. (3 pages, in English).

Arefnia, Ali, et al. "Comparative Study on the Effect of Tire-Derived Aggregate on Specific Gravity of Kaolin." Electronic Journal of Geotechnical Engineering 18 (2013): 335-44.

Kesavan, Jana, et al. "Density Measurements of Materials Used in Aerosol Studies". Edgewood Chemical Biological Center Aberdeen Proving Ground MD, 2000.

International Search Report and Written Opinion issued on May 31, 2021 in counterpart International Patent Application No. PCT/US2020/067626 (21 pages, in English).

* cited by examiner

DEVICES AND METHODS FOR DELIVERING POWDERED AGENTS

CROSS-REFERENCE TO RELATED APPLICATION(S)

This application claims the benefits of priority to U.S. Provisional Patent Application No. 62/957,519, filed Jan. 6, 2020, the entirety of which is incorporated herein by reference.

TECHNICAL FIELD

Various aspects of the present disclosure relate generally to devices and methods for delivering agents. More specifically, in embodiments, the present disclosure relates to devices for delivery of powdered agents, such as hemostatic agents.

BACKGROUND

In certain medical procedures, it may be necessary to stop or minimize bleeding internal to the body. For example, an endoscopic medical procedure may require hemostasis of bleeding tissue within the gastrointestinal tract, for example in the esophagus, stomach, or intestines.

During an endoscopic procedure, a user inserts a sheath of an endoscope into a body lumen of a patient. The user utilizes a handle of the endoscope to control the endoscope during the procedure. Tools are passed through a working channel of the endoscope via, for example, a port in the handle, to deliver treatment at the procedure site near a distal end of the endoscope. The procedure site is remote from the operator.

To achieve hemostasis at the remote site, a hemostatic agent may be delivered by a device inserted into the working channel of the endoscope. Agent delivery may be achieved through mechanical systems, for example. Such systems, however, may require numerous steps or actuations to achieve delivery, may not achieve a desired rate of agent delivery or a desired dosage of agent, may result in the agent clogging portions of the delivery device, may result in inconsistent dosing of agent, or may not result in the agent reaching the treatment site deep within the GI tract. The current disclosure may solve one or more of these issues or other issues in the art.

SUMMARY

Each of the aspects disclosed herein may include one or more of the features described in connection with any of the other disclosed aspects.

In one example, a device for delivering an agent may comprise a chamber for receiving agent through an agent inlet; and a body received within the chamber. The body may be movable in first and second directions along a longitudinal axis of the chamber. In a first configuration of the body, an amount of the agent may flow into the chamber via the agent inlet. In a second configuration of the body, the agent may be prevented from flowing into the chamber via the agent inlet. When the body is transitioned from the first configuration to the second configuration, the amount of the agent may be moved from a first position along the longitudinal axis of the chamber to a second position along the longitudinal axis of the chamber.

Any of the devices described herein may have any of the following features. When the body is in the second configuration, fluid may flow into the chamber via a fluid inlet and combines with the amount of the agent. The fluid inlet may be located between (a) an outlet for delivering the fluid combined with the amount of the agent from the chamber and (b) the agent inlet. A spring may be attached to the body. The body may transition from the first configuration to the second configuration due to a restorative force of the spring. The device may include a yoke and at least one track for receiving the yoke. In the first configuration, the yoke may contact the body. The body may transition from the first configuration to the second configuration when the yoke ceases contacting the body. A gear may have gear teeth, wherein the body includes body teeth for mating with the gear teeth. Only a portion of a circumference of the gear may include gear teeth, and wherein the body transitions from the first configuration to the second configuration when the gear teeth do not engage with the body teeth. An arm may have a finger and a guide may have a protrusion. The body may transition from the first configuration to the second configuration when the finger contacts the protrusion. A source of agent may be coupled to the body. The chamber is a first chamber, further comprising a second chamber, wherein the body defines a body opening, wherein, in the first configuration, the body opening is in fluid communication with the agent inlet, and wherein, in the second configuration, the body opening is in not in fluid communication with the agent inlet and is in fluid communication with a chamber opening between the first chamber and the second chamber. The body may be connected to an arm via a hinge. The arm may be connected to a trigger. Depressing the trigger may cause the arm to pivot and cause the body to move in the first direction. Releasing the trigger may cause the arm to pivot and cause the body to move in the second direction, transitioning the body from the first configuration to the second configuration. The chamber opening may be proximal of the agent inlet.

In another example, a device for delivering an agent may comprise: a source of agent; a mixing chamber in fluid communication with the source of agent via an agent inlet; and a body received within the mixing chamber and movable between a first configuration and a second configuration. In the first configuration, a distal end of the body is proximal of the agent inlet, and the agent flows from the agent inlet into the mixing chamber. When the body is transitioned from the first configuration to the second configuration, the distal end of the body may push the agent distally toward a fluid inlet. In the second configuration, the distal end of the body may be distal to the agent inlet and proximal of the fluid inlet, such that the agent is permitted to mix with fluid received form the fluid inlet.

Any of the devices described herein may have any of the following features. The body may be attached to a spring. A restoring force of the spring may cause the body to transition from the first configuration to the second configuration.

In another example, a device for delivering an agent may comprise a first chamber in fluid communication with an agent inlet; a second chamber in fluid communication with a fluid inlet; and a wall formed between the first chamber and the second chamber. The wall may define a chamber opening between the first chamber and the second chamber. A body may be received within the first chamber and define a body opening. The body may be configured to be transitioned from a first configuration, in which the body opening is in fluid communication with the agent inlet and not in fluid communication with the chamber opening, to a second configuration, in which the body opening is in fluid communication with the chamber opening and not in fluid communication with the agent inlet.

Any of the devices disclosed herein may have any of the following features. The body may be connected to a pivotable arm via a hinge. The pivotable arm may be connected to a trigger. The trigger may be operative to control a flow of fluid through the fluid inlet.

It may be understood that both the foregoing general description and the following detailed description are exemplary and explanatory only and are not restrictive of the invention, as claimed. As used herein, the terms "comprises," "comprising," or any other variation thereof, are intended to cover a non-exclusive inclusion, such that a process, method, article, or apparatus that comprises a list of elements does not include only those elements, but may include other elements not expressly listed or inherent to such process, method, article, or apparatus. The term "distal" refers to a direction away from an operator, and the term "proximal" refers to a direction toward an operator. The term "exemplary" is used in the sense of "example," rather than "ideal." The term "approximately," or like terms (e.g., "substantially"), includes values+/−10% of a stated value.

BRIEF DESCRIPTION OF THE DRAWINGS

The accompanying drawings, which are incorporated in and constitute a part of this specification, illustrate aspects of the present disclosure and together with the description, serve to explain the principles of the disclosure.

DETAILED DESCRIPTION

Figure 1:
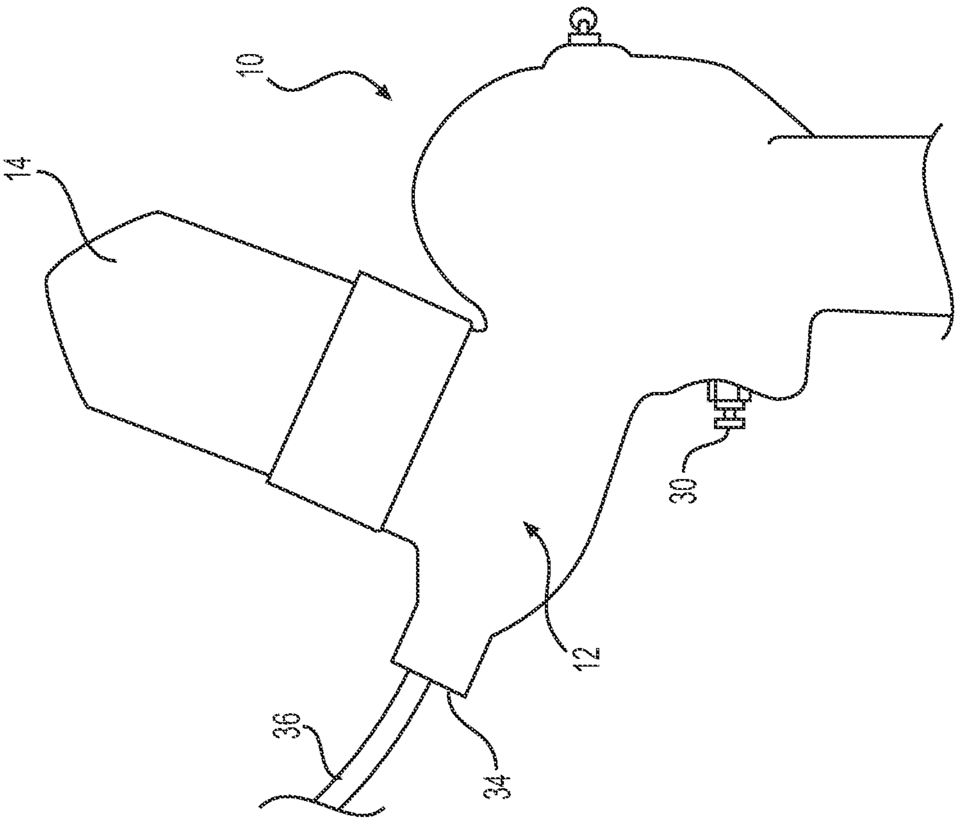
FIG. 1 shows an exemplary delivery device.

Embodiments of this disclosure relate to a metering/actuation mechanism to deliver an agent (e.g., a powdered agent) from a delivery system to a site of a medical procedure. The actuation mechanism may deliver a predetermined amount of powder or particles in a desired form to be propelled by, or combined with, a fluid, for delivery to a treatment site.

FIG. 1A shows a delivery system 10, which may be a powder delivery system. Delivery system 10 may include a body 12. Body 12 may include or may be configured to receive an enclosure 14 (or other source) storing an agent. Enclosure 14 may be coupled to body 12 for providing agent to body 12, or a lid/enclosure of the agent may be screwed onto, or otherwise coupled to, enclosure 14 for supplying the agent to enclosure 14. The agent may be, for example, a powdered agent, such as a hemostatic agent. The agent may alternatively be another type of agent or material or form of agent (e.g., a liquid or gel agent) and may have any desired function. Enclosure 14 may be removably attached to other components of delivery system 10, including components of body 12. Body 12 may have a variety of features, to be discussed in further detail herein. U.S. patent application Ser. No. 16/589,633, filed Oct. 1, 2019, the disclosure of which is hereby incorporated by reference in its entirety, discloses features of exemplary delivery devices and systems. The features of this disclosure may be combined with any of the features described in the above-referenced application. The features described herein may be used alone or in combination and are not mutually exclusive. Like reference numbers and/or terminology are used to denote similar structures, when possible.

A combination of agent and fluid may be delivered from outlet 34 of body 12. As used herein, the terms "distal"/"first direction" may refer to a direction toward outlet 34, and the terms "proximal"/"second direction" may refer to the opposite direction. Outlet 34 may be in fluid communication with a catheter 36 or other component for delivering the combination of agent and fluid to a desired location within a body lumen of a patient.

Figure 2A:
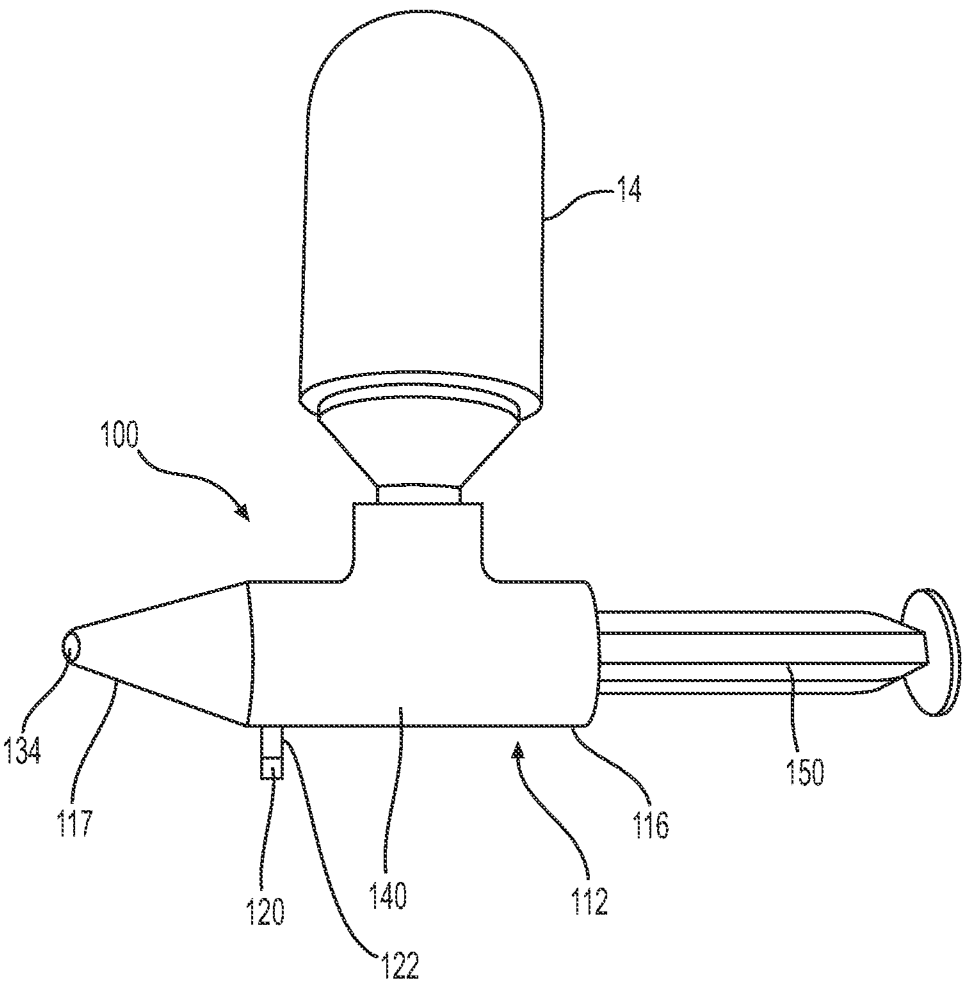
FIGS. 2A-7B show various example actuation mechanisms for use in a delivery device, including in the delivery device of FIG. 1.
Figure 2B:
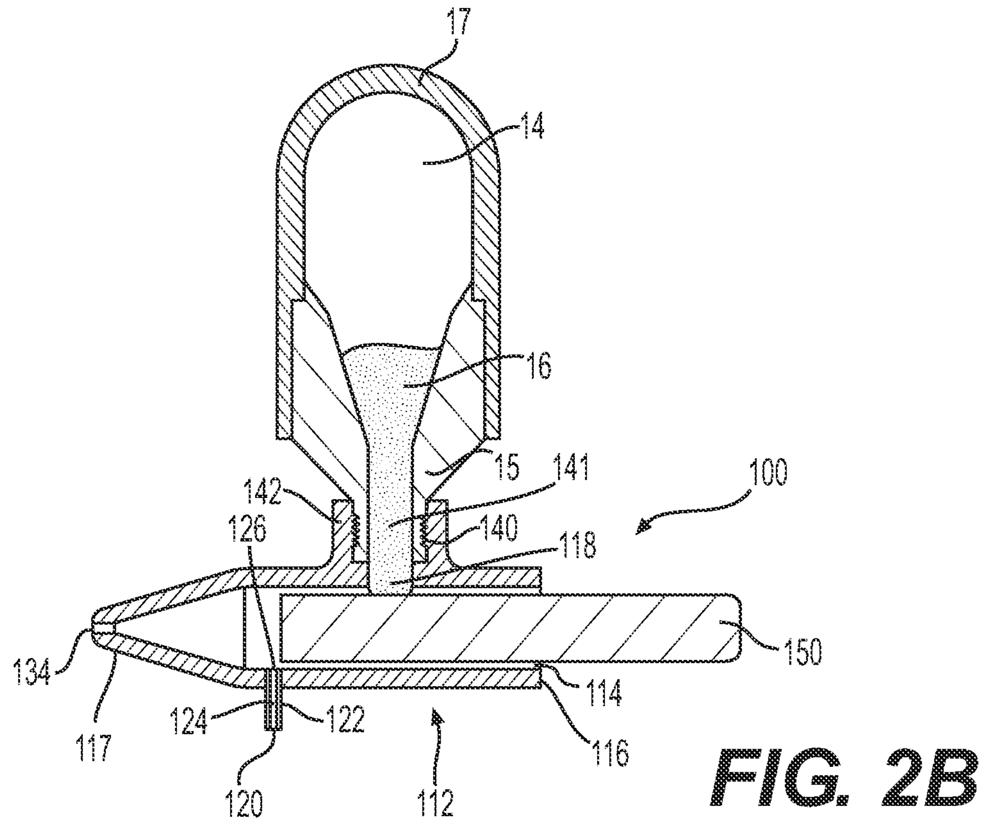
Figure 2C:
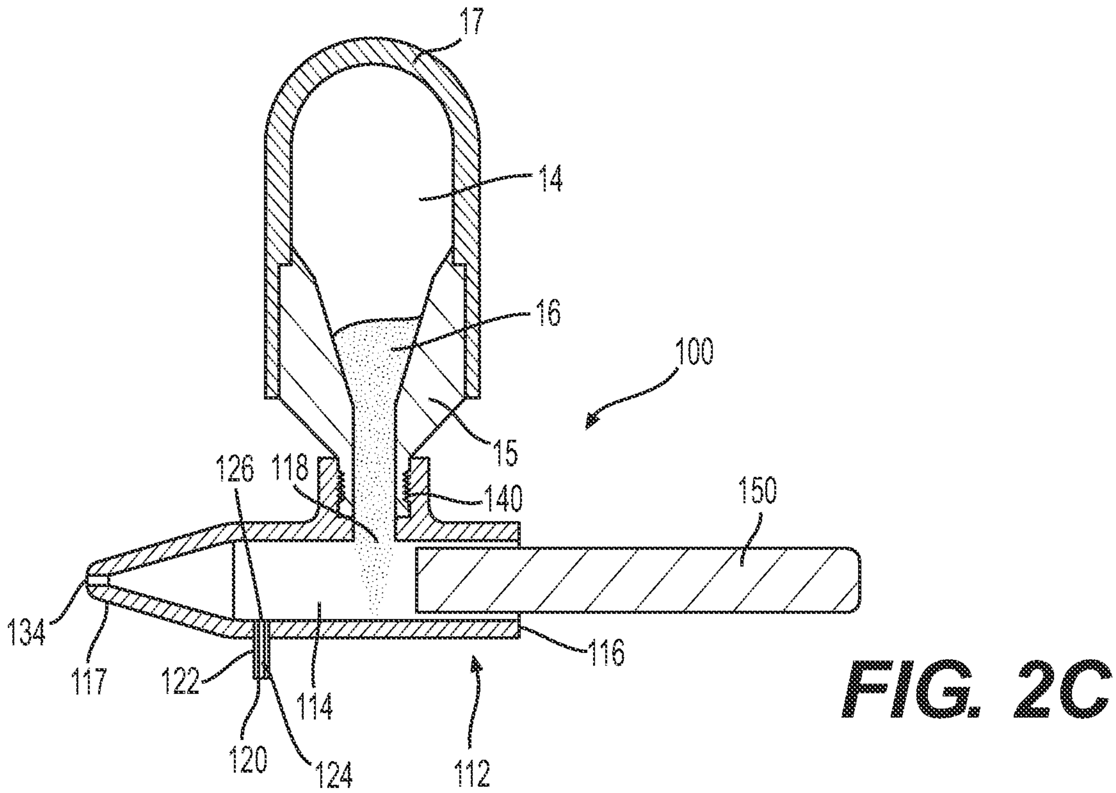

FIGS. 2A-2C show an exemplary metering assembly 100 for use in agent delivery system 10. Metering assembly 100 may include a body 112, which may have any of the properties of body 12, above. Body 112 may define a lumen or chamber 114 (see FIGS. 2B-2C), which may extend from a first/proximal end 116 of body 112 to a second/distal end 117 of body 112. Near second end 117, walls of body 112 may taper toward a central longitudinal axis of lumen 114, causing a cross-sectional width of lumen 114 to also taper. For example, walls of body 112 may form an approximately conical shape. Lumen 114 may terminate at second end 117 in an outlet 134, which may have any of the properties of outlet 34.

Body 112 may include a protrusion 122, which may define a lumen 124 in fluid communication with lumen 114 via an opening 126. An end of lumen 124 opposite opening 126 may define a fluid inlet 120. Protrusion 112 may be configured to be connected to a source of fluid. For example, protrusion 112 may include ridges, grooves, or other features to facilitate connection with a source of fluid. When a source of fluid is connected to protrusion 112, the source of fluid may be in fluid communication with fluid inlet 120, lumen 124, opening 126, lumen 114, and outlet 134.

Body 112 may also include a receptacle 140, which may be defined by walls 142 that protrude radially outward from body 112 in a direction perpendicular to a longitudinal axis of lumen 114. Receptacle 140 may be in fluid communication with lumen 114 via an agent inlet 118. Receptacle 140 of body 112 may be configured to receive a enclosure 14 (or other source) storing an agent 16 (FIGS. 2B-2C). Enclosure 14 may include a funnel 15 and a cap 17. Cap 17 may be fixedly or removably attached to a remainder of enclosure 14 via any suitable mechanism (e.g., by screwing cap 17 onto threads on another portion of enclosure 14). Funnel 15 may have an angle (between an inner side surface of funnel 15 and a line perpendicular to a longitudinal axis of enclosure 14) that is greater than an angle of repose of agent 16. An angle of repose of agent 16 may be an angle formed by a cone-like pile of agent 16 as agent 16 flows through an orifice and collects on a surface in the cone-like pile. The angle of repose may be the angle between the surface onto which the agent 16 flows and a surface of the cone-like pile. The angle of repose may be related to friction or resistance to movements between particles of agent 16. Because funnel 15 may have an angle greater than the angle of repose of agent 16, agent 16 may flow freely through funnel 15 due to a force of gravity.

Enclosure 14 may have an opening 141 formed at an end of enclosure 14 received by receptacle 142. Enclosure 14 includes threads, grooves, ridges, or other structures for mating with corresponding features of walls 142 or other portions of body 112. For example, enclosure 14 may be screwed into receptacle 140. When enclosure 14 is received in receptacle 140, enclosure 14 may be in fluid communication with lumen 114 via opening 141 and agent inlet 118.

Moving longitudinally along lumen 114 from first end 116 of body 112 to second end 117 of body 112, agent inlet 118 may be closest to first end 116. Fluid inlet 120 may be between agent inlet 118 and outlet 134. Agent outlet 134 may be at second end 117. Agent inlet 118 and fluid inlet 120 may be offset from one another along a perimeter of lumen 114. For example, agent inlet 118 and fluid inlet 120 may be opposite one another (e.g., diametrically opposed to one another), in addition to being longitudinally offset from one another. Alternatively, agent inlet 118 and fluid inlet 120 may be aligned along a longitudinal line extending axially down an outside of body 112 (i.e., on the same side of body 112, with no circumferential offset).

A plunger or other body 150 may be slidably received within lumen 114. The combination of plunger 150 and body 112 (including lumen 114) may function like a syringe. Plunger 150 may be slidable along an entire length of lumen 114 that has a cross-sectional width large enough to receive plunger 150. For example, plunger 150 may be slidable from the portion of lumen 114 near first end 116 up until tapering walls of body 112 near outlet 134 prevent further advancement of plunger 150. Surfaces defining lumen 114 may alternatively have protrusions (not shown) extending into lumen 114 that prevent passage of plunger 150 past the protrusions. For example, such a protrusion may extend into lumen 114 proximally of fluid inlet 120/opening 126 to prevent plunger 150 from moving distally past fluid inlet 120/opening 126.

FIG. 2B shows plunger 150 in a first configuration, and FIG. 2C shows plunger 150 in a second configuration. In the first configuration (FIG. 2B), a distal end of plunger 150 may be proximal of fluid inlet 120/opening 126, but distal to agent inlet 118. Plunger 150 may include seals or may be formed of a material such as to create a seal with surfaces defining lumen 114 (such as seals 668, included on plunger 650, described below). Therefore, agent 16 may be unable to pass plunger 150 to enter lumen 114, when plunger 150 is in the first configuration. If fluid is flowing through fluid inlet 120, fluid may be able to enter lumen 114 and pass out of outlet 134. Fluid may not be able to move proximally, past plunger 150, due to seals formed between plunger 150 and surfaces defining lumen 114. Additionally or alternatively, opening 126 or another portion of metering assembly 100 may be configured so as to direct fluid 120 in a generally distal direction after it enters lumen 114, so that an appreciable amount of fluid is prevented from passing proximally.

In the second configuration (FIG. 2C), a distal end of plunger 150 may be proximal of fluid inlet 120/opening 126 and agent inlet 118. Therefore, both fluid and agent 16 may be able to pass into lumen 114 via fluid inlet 120 and agent inlet 118, respectively. Fluid may or may not flow while plunger 150 is in the second configuration. If fluid flows in the second configuration, fluid may be directed distally, as discussed above, so that fluid may not mix with agent 16 in the second configuration because agent 16 is located proximally of fluid inlet 120. Alternatively, a flow of fluid may be such that fluid does mix with agent 16 in the second configuration (e.g., fluid may be permitted to flow proximally).

An operation of metering assembly 100 will now be described. FIGS. 3A-5B show various actuation mechanisms to transition plunger 150 between the first configuration and the second configuration. In operation, plunger 150 may initially be positioned in the first configuration (FIG. 2B), using any of the actuation mechanisms described herein, with respect to FIGS. 3A-5B. In the first configuration, fluid may not flow through fluid inlet 120. Alternatively, fluid may flow through fluid inlet 120, and a flow of fluid, without agent 16, may be delivered via outlet 134.

Plunger 150 may then be transitioned to the second configuration (FIG. 2C), in which agent 16 may enter lumen 114. A time in which plunger 150 is maintained in the second configuration (or a time in which a distal end of plunger 150 is proximal to agent inlet 118) may determine an amount of agent 16 which is able to enter lumen 114 via agent inlet 118. The desired amount of agent 16 may form a dose of agent 16. While plunger 150 is in the second configuration, fluid may or may not enter lumen 114 via fluid inlet 120. As discussed above, if fluid enters lumen 114 while plunger 150 is in the second configuration, fluid may or may not mix with agent 16 while plunger is in the second configuration, depending, at least in part, on a flow pattern of the fluid.

Then, plunger 150 may be transitioned back to the first configuration (FIG. 2B). A distal end of plunger 150 may push agent 16 within lumen 114 distally, toward fluid inlet 120/opening 126. Fluid may flow into lumen 114 via fluid inlet 120/opening 126. Agent 16 may mix with the fluid, and the combined agent 16 and fluid may exit lumen 114 via outlet 134.

Flow of fluid through fluid inlet 120 may be controlled by a valve, such as a button valve (not shown). The same actuation mechanism (e.g., actuation mechanism 30) may control both movement of plunger 150 and the valve, or separate actuation mechanisms may be used. For example, actuation mechanism 30 (e.g., a trigger) may be configured to transition plunger 150 to the second configuration (FIG. 2C) without a flow of fluid yet being activated (e.g., without opening the valve). Plunger 150 may then be transitioned to the first configuration (FIG. 2B), and shortly before, during, or after the transition to the first configuration, a flow of fluid through fluid inlet 120 may be activated to deliver the agent 16 within lumen 114 via outlet 134. When actuation mechanism 30 is released by a user, fluid flow through fluid inlet 120 may cease.

Fluid inlet 120 may have features to prevent flow of agent 16 from lumen 114 into fluid inlet 120. For example, a filter or sieve of appropriate size may be disposed in lumen 114, opening 126, or fluid inlet 120, which prevents agent 16 from flowing through the filter or sieve. Additionally or alternatively, an orientation of fluid inlet 120 may be such that gravity prevents agent 16 from flowing into fluid inlet 120. For example, fluid inlet 120 may be above opening 126, or opening 126 may be formed in a top surface of body 112. The terms above, top, etc. may refer to an orientation with respect to the force of gravity, rather than an orientation depicted in the Figures.

A venting hole (not shown) may be formed in body 112 to allow air to flow into lumen 114 as plunger 150 is pulled proximally, to prevent formation of vacuum effects in lumen 114 due to movement of plunger 150, which may have a sealed contact with surfaces defining lumen 114. Such a venting hole may prevent suction effects in catheter 36 (FIG. 1).

As described above, FIGS. 3A-5B show exemplary actuation assemblies, which may be used to transition plunger 150 between the first and second configurations of FIGS. 2B-2C. Where possible, like reference numbers are used below to indicate like structures.

Figure 3A:
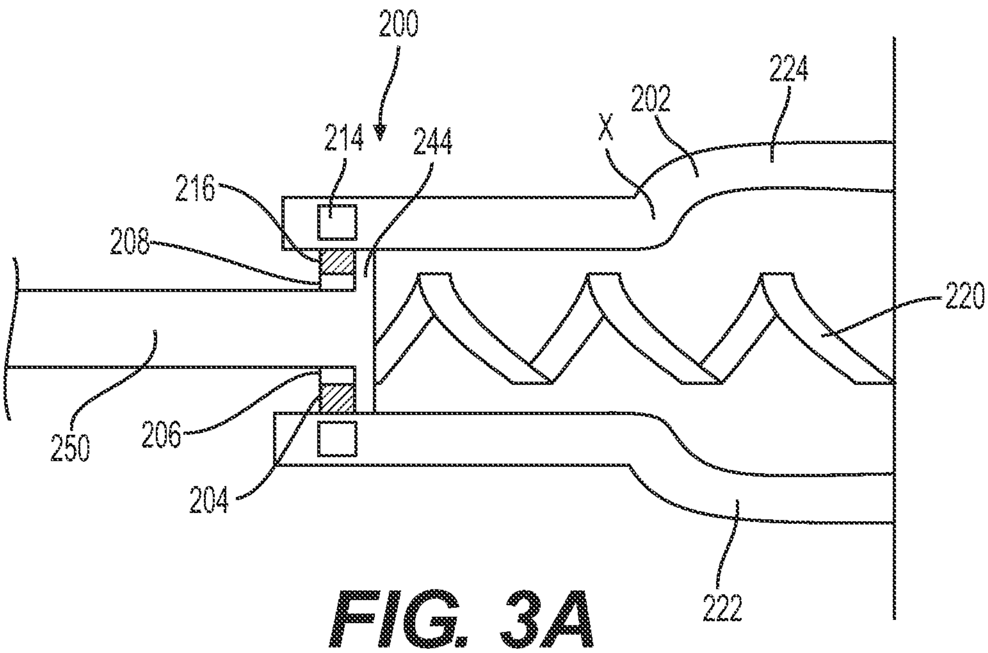
Figure 3B:
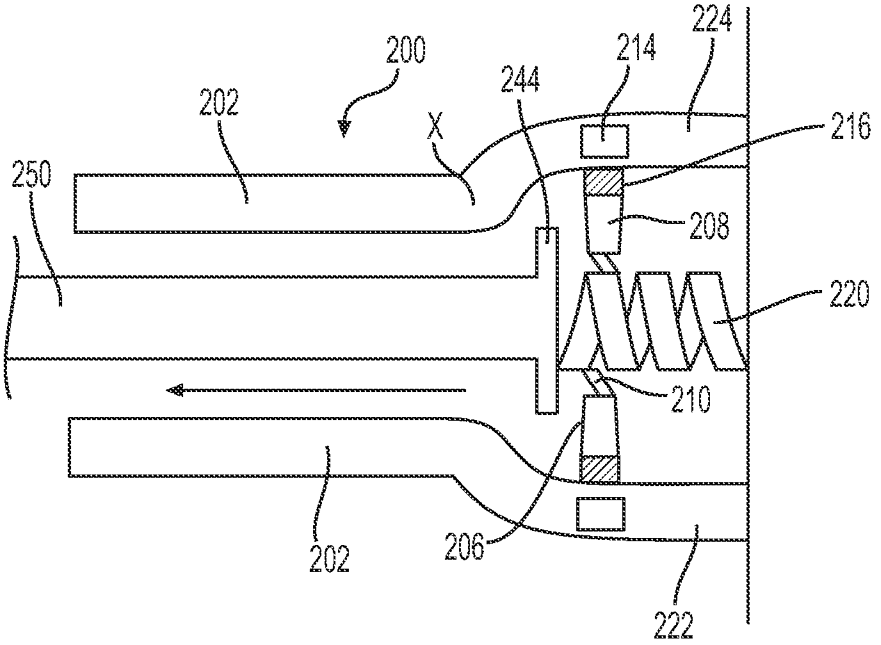
Figure 3D:
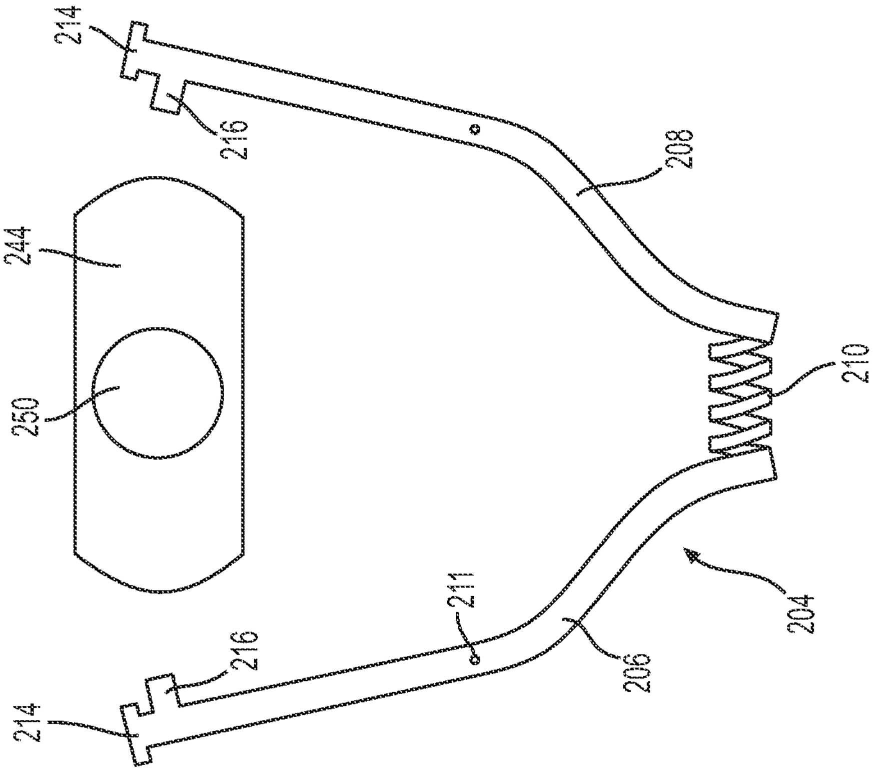
Figure 3C:
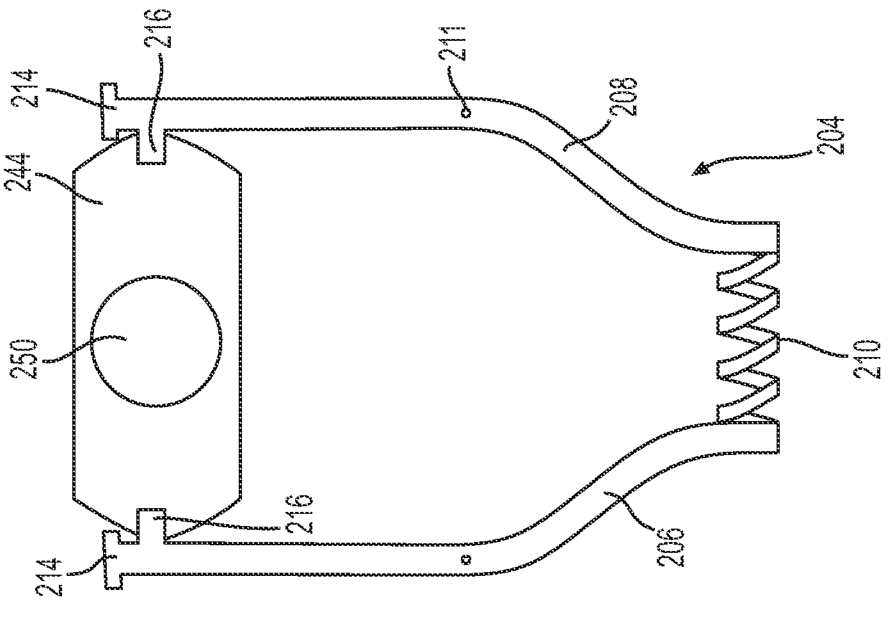

FIGS. 3A-3D show a first actuation assembly 200. Actuation assembly 200 may be used to move a plunger or other body 250, which may have any of the features of plunger 150, in the first direction or second direction (proximally or distally) within lumen 114 of metering assembly 100. As shown in FIGS. 3C-3D, actuation assembly 200 may include a yoke 204. Yoke 204 may be configured to move proximally and distally along tracks 202 (FIGS. 3A-3B). Yoke 204 may include a first arm 206 and a second arm 208, which may be joined by a spring 210. Spring 210 may be fixed to ends of first arm 206 and second arm 208. Spring 210 may bias first arm 206 and second arm 208 so that the portions of first arm 206 and second arm 208 connected to spring 210 are a predetermined distance apart from one another. A function of spring 210 will be discussed in further detail below. Arms 206, 208 may be pivotable about pivot pins 211, as discussed in further detail below. Alternatively, spring 210 and pivot pins 211 may be omitted, and first arm 206 and second arm 208 may be formed of shape memory material and/or may be joined together by any suitable structure or formed from a single, unitary piece of material.

Runners 214 may be disposed at an end of arms 206, 208 opposite the ends connected to spring 210. Runners 214 may be configured to be received within tracks 202. Tracks 202 may include openings (not shown) that receive arms 206, 208. Runners 214 may project outward perpendicularly to longitudinal axes of arms 206, 208, to retain runners 214 in tracks 202. Runners 214 may be wider than the openings, to prevent arms 206, 208 from disengaging from tracks 202.

Arms 206, 208 may also include tabs 216 for contacting plunger 250. Tabs 216 may project from arms 206, 208, toward the other of arms 206, 208. Tabs 216 may be disposed near runners 214. Arms 206, 208 may each be formed of a single, unitary piece of material, including runners 214 and tabs 216. Alternatively, runners 214 and/or tabs 216 may be formed of another material and fixed to arms 206, 208.

As shown in FIGS. 3A and 3B, tracks 202 may include two tracks, 222, 224. Tracks 222, 224 may have symmetrical shapes. Tracks 222, 224 may be shaped so that tracks 222, 224 are closer to one another at a distal portion of tracks 222, 224 than at a proximal portion of tracks 222, 224. For example, tracks 222, 224 may be a first distance apart at a distal portion of tracks 222, 224. Tracks 222, 224 may be a second, larger distance apart at a proximal portion of tracks, 222, 224. Tracks 222, 224 may have a constant separation (e.g., the first distance) for a portion of tracks 222, 224. For example, a length of tracks 222, 224 that are separated by the first distance may correspond to a distance that plunger 250 is to be moved proximally. Tracks 222, 224 may have an inflection point X at which tracks 222, 224 bend such that a distance between tracks 222, 224 increases. An increase in distance between tracks 222, 224 may be gradual or may be sharp. Tracks 222, 224 may be curved, as shown in FIGS. 3A-3B, or may be made of numerous straight segments. Tracks 222, 224 may have a constant separation (e.g., the second distance) proximal of the inflection point, or a separation of tracks 222, 224 may vary.

Runners 214 may be slidably disposed in tracks 222, 224, so that runners 214 may slidably move proximally and distally along tracks 222, 224. Runners 214 may be retained within tracks 222, 224 by any suitable mechanism. For example, tracks 222, 224 may have walls that retain runners 214.

A spring 220 may extend from a proximal end of plunger 250 (e.g., near flange 244). Spring 220 may be fixedly coupled to plunger 250 and to another surface of delivery system 100, proximal to plunger 250.

As shown in FIG. 3A, in a first configuration, runners 214 may be disposed near the distal end of tracks 222, 224, where the tracks 222, 224 are relatively closer together than they are at a more proximal portion of tracks 222, 224. The configuration of FIG. 3A may correspond to the configuration of plunger 150 in FIG. 2A. The positioning of yoke 204 in the first configuration is shown in FIG. 3C. In the first configuration, tabs 216 may engage with plunger 250. For example, plunger 250 may include a flange 244 which extends radially outward at a proximal portion of plunger 250. Tabs 216 may be positioned distally of plunger 250 (e.g., distally of flange 244). Spring 210 may be at its resting length in the first configuration. In the first configuration, spring 220 may be at its relaxed length or at approximately its relaxed length. Spring 220 may not exert a force on plunger 250 in the first configuration.

Activation of actuation mechanism 30 (e.g., a trigger or lever) may cause yoke 204 to move in the second direction (the proximal direction), riding along tracks 222, 224. For example, yoke 204 may be mounted in a structure (not shown) such as a lever or a trigger, which may be activated/pulled by a hand or finger squeeze. Pivot pins 211 may be used to mount yoke 204 to the structure such that arms 206, 208 may pivot about pivot pins 211. Tabs 216 may exert a force on flange 244 or another portion of plunger 250 in the second direction (the proximal direction). The force of tabs 216 on plunger 250 may cause plunger 250 to move in the second direction, along with yoke 204. Plunger 250 may exert a force on spring 220, causing spring 220 to compress. As plunger 250 moves proximally, agent 16 may begin to flow through agent inlet 118, as described above with respect to FIGS. 2A-2C.

When yoke 204 reaches inflection point X, arms 206, 208 of yoke 204 may begin to separate from one another and pivot about pivot pins 11. When arms 206, 208 are sufficiently separated, tabs 216 will cease contacting flange 244 or another portion of plunger 250, as shown in FIGS. 3B and 3D. Just prior to a loss of contact between tabs 216 and flange 244, plunger 250 may be in a configuration like that of plunger 150 in FIG. 2C. Spring 210 may be compressed so that it has a length that is shorter than its relaxed state.

FIG. 3B shows a second configuration of actuation mechanism 200, after tabs 216 have lost contact with plunger 250. Once tabs 216 no longer exert a force on plunger 250, the force from compressed spring 220 may push plunger 250 in the first direction (distally), shown by the arrow in FIG. 3B. A force of spring 220 may transition plunger 250 back to a position corresponding to the configuration of plunger 150, shown in FIG. 2B. This action may result in mixing of agent 16 with fluid, as described above with regard to FIGS. 2A-2C. Motion of plunger 250 in the first direction may cease once spring 220 is in a relaxed configuration (and no longer exerts a force on plunger 250), once plunger 250 contacts a stopping mechanism (not shown), or due to some other condition.

When actuation mechanism 30 is released, yoke 204 may move in the first direction (distally). Runners 214 may ride tracks 222, 224 in the first direction. Spring 210 may expand, returning to its natural length. Yoke 204 may then re-engage with plunger 250. For example, tabs 216 may be flexible or bendable only in the second direction and include shape memory material or a spring, so that, as tabs 216 pass flange 244 of plunger 250, tabs 216 are temporarily pressed against arms 206, 208, until tabs 216 are past flange 244 of plunger 250. Tabs 216 may then return to their expanded configuration due to shape memory properties or a spring. Tabs 216 may then engage with plunger 250, distally of flange 244 or another portion of plunger 250. Alternatively or additionally, a geometry of yoke 204 and plunger 250 may be such that tabs 216 may slip past flange 244. Once tabs 216 engage with plunger 250, actuation assembly 200 may again be in the first configuration of FIG. 3A (corresponding to the position of plunger 150 in FIG. 2B).

Figure 4A:
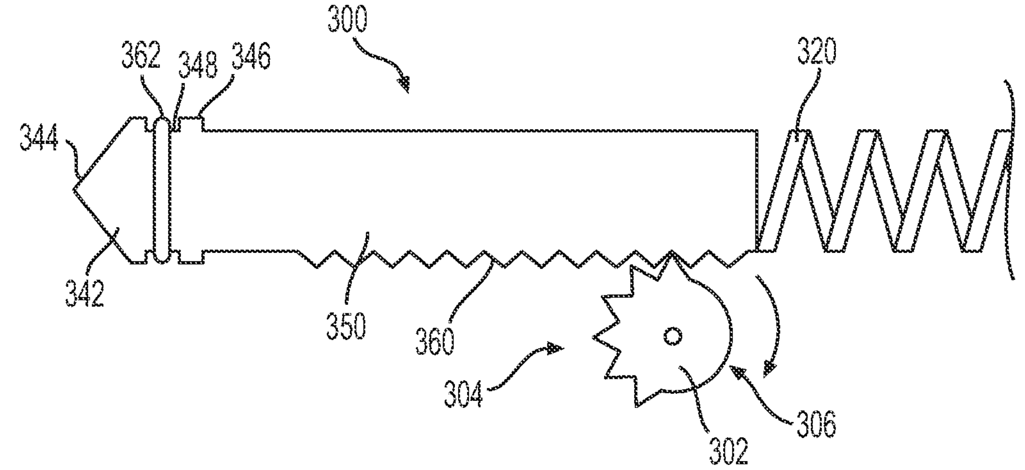
Figure 4B:
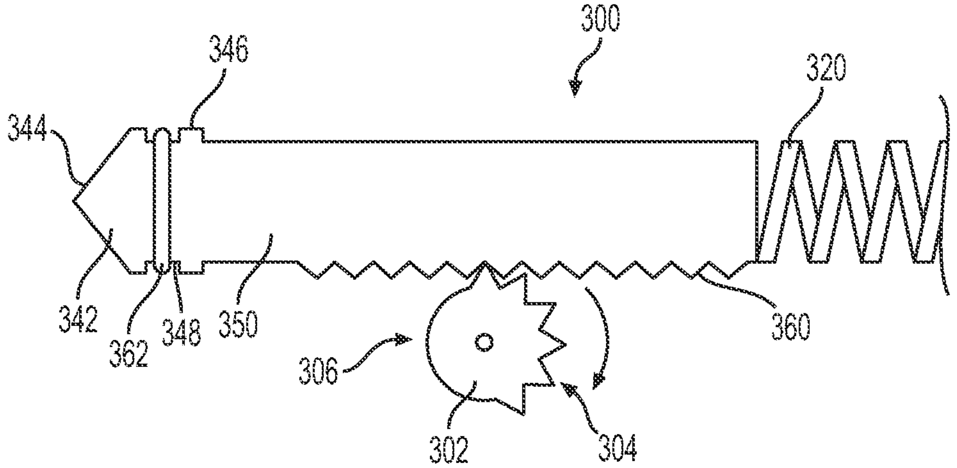
Figure 4C:
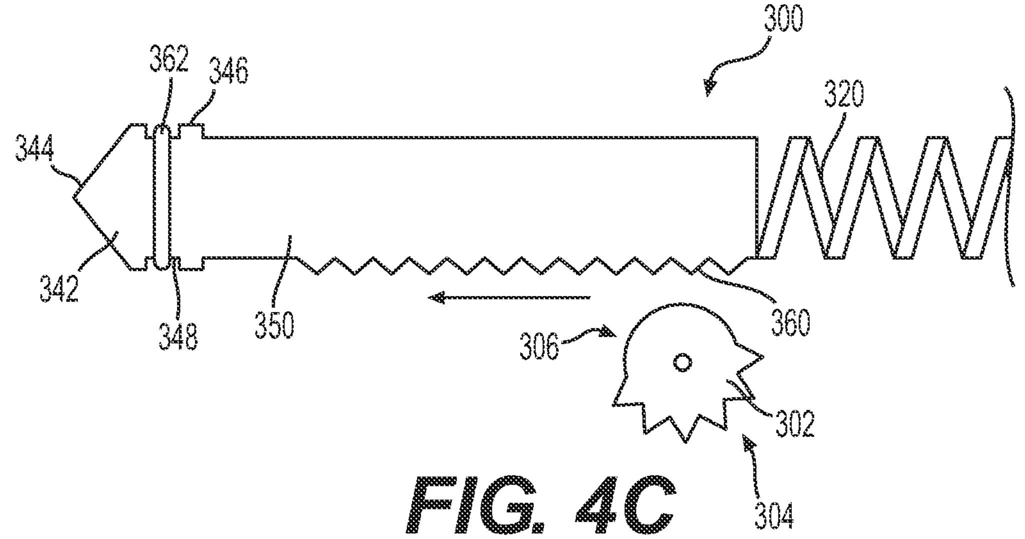

FIGS. 4A-4C show another actuation assembly 300. Actuation assembly 300 may be used to move a plunger or other body 350, which may have any of the features of plunger 150 or 250, proximally or distally within lumen 114 of metering assembly 100. Actuation assembly 300 may include a round gear 302. Gear 302 may have a toothed portion 304 and a smooth portion 306. As shown in FIG. 4A, toothed portion 304 and smooth portion 306 may each occupy approximately one half of the circumference of gear 302. Alternatively, toothed portion 304 and smooth portion 306 may occupy different proportions of a circumference of gear 302. Although one toothed portion 304 and one smooth portion 306 are shown in FIG. 4, other numbers of toothed portions 304 and smooth portions 306 may be used.

Plunger 350 may include teeth 360, which are configured to engage with teeth of toothed portion 304. As shown in FIG. 4A-4C, teeth 360 may extend along only a portion of a length of plunger 350. Alternatively, teeth 360 may extend along an entire length of plunger 350. Teeth 360 may be formed only on one side of plunger 350 (a side facing gear 302) or may surround an entirety of plunger 350. A spring 320 may be attached to an end of plunger 350 that is opposite a distal end 342 of plunger 350 (i.e., a proximal end of plunger 350). A second end of spring 320 may be fixedly coupled to another portion of delivery system 10.

Gear 302 may be disposed on an opposite side of body 140 (FIG. 2A-2C) from enclosure 14 (below body 140 in FIGS. 2A-2C). An opening (e.g., a longitudinal opening or a slit) may be formed through a wall of body 140, so that gear 302 may extend through the wall and into lumen 114, where plunger 350 is located. Alternatively, teeth 360 of plunger 350 may extend through the opening.

A protruding portion 346 of plunger 350 near distal portion 342 of plunger 350 and proximal to a tapered tip 344 of plunger 350 may have a larger cross section than a remainder of plunger 350 proximal to protruding portion 346. Protruding portion 346 may include a recess 348. Recess 348 may receive a seal 362, such as an O-ring seal. Seal 362 may prevent undesired movement of agent 16 or fluid. Alternatively, other portions of protruding portion 346 or plunger 350 may receive a seal. Although one protruding portion 346 and seal 362 is shown, plunger 350 may include other protruding portions and seals (e.g., proximally of teeth 360). Positioning of seal(s) may be chosen so as to facilitate the flow of agent 16 and fluid, as described with respect to FIGS. 2A-2C. Distal portion 342, tapered tip 344, and/or protruding portion 346 may include a rubber or other material that provides a gasket-like or O-ring like seal with a surface of lumen 14 (or an alternative feature) that receives plunger 350.

Before a user activates actuation mechanism 30, plunger 350 may be in the configuration shown in FIG. 4A, which corresponds to the configuration of plunger 150 in FIG. 2B. Gear 302 may be positioned such that, when gear 302 begins to rotate clockwise, toothed portion 304 will engage with teeth 360. Spring 320 may be in a neutral position, at its natural length.

When a user activates actuation mechanism 30, gear 302 may begin to rotate about its axis. Toothed portion 304 may engage with teeth 360, exerting a force on plunger 350 in the second (proximal) direction, causing plunger 350 to move in the second (proximal) direction. As plunger 350 moves in the second direction, it may compress spring 320, which may exert a restorative force on plunger 350 in the first direction. Plunger 350 may continue to move in the second direction until it reaches the configuration of FIG. 4B. The configuration of FIG. 4B may correspond to the configuration of plunger 150 in FIG. 2C. After tip 344 is proximal of agent inlet 118, agent 16 may begin to flow into lumen 114, as discussed above.

As gear 302 continues to rotate, a last tooth of toothed portion 304 may disengage from teeth 360, and smooth portion 306 may face plunger 350. As shown in FIG. 4C, the restorative force of spring 320 may exert a force on plunger 350 in the first direction, causing plunger 350 to move in the first direction, until it again reaches the configuration shown for plunger 150 in FIG. 2B. The movement of plunger 350 in the first direction may push agent 16 in the first direction. Actuation mechanism 30 may be configured so that a flow of fluid through fluid inlet 120 is activated when plunger 350 is moving in the first direction. Agent 16 may combine with fluid from fluid inlet 120, as described above, and may be delivered via outlet 134.

After actuation mechanism 30 is released, gear 302 may return to a configuration in which toothed portion 304 is ready to engage with teeth 360. For example, a ratcheting mechanism may be used to position gear 302 in the configuration of FIG. 4A. Alternatively, gear 302 may continue to rotate as plunger 350 moves in the first direction and may be configured so as to align toothed portion 304 in the position of FIG. 4A so that it will engage teeth 360 when actuation mechanism 30 is again activated. Alternatively, gear 302 may be biased to return gear 302 to the configuration shown in FIG. 4A.

Figure 5A:
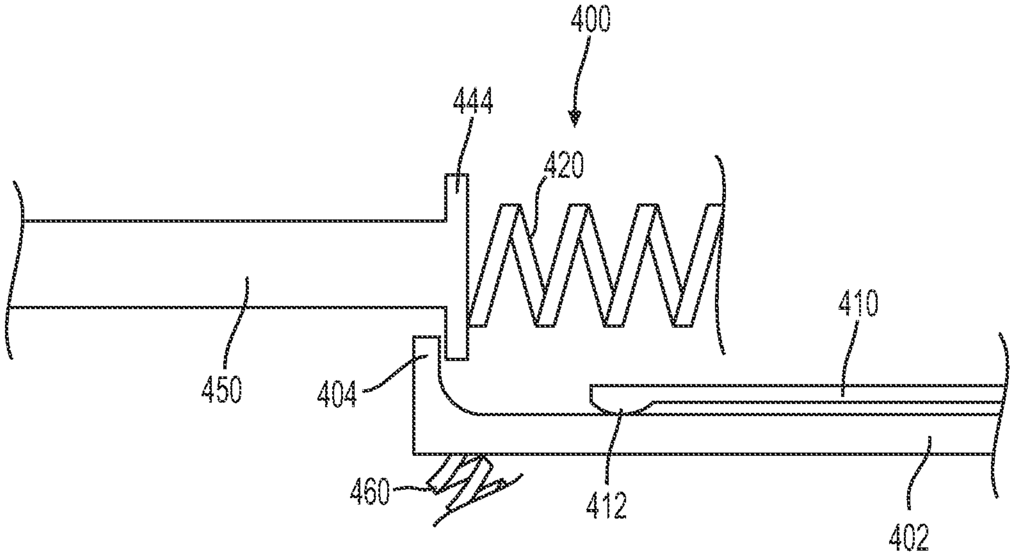
Figure 5B:
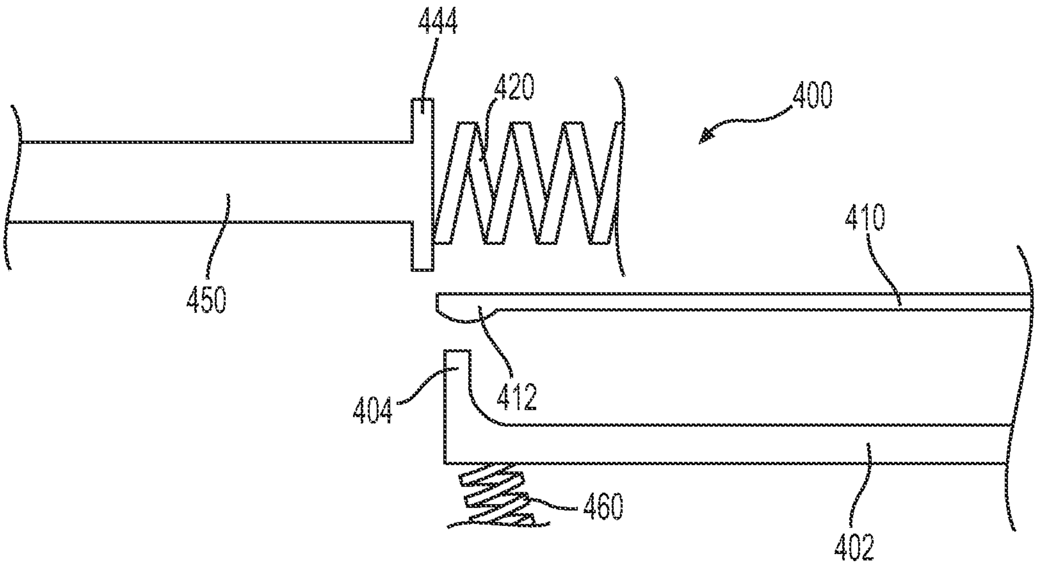

FIGS. 5A-5B show another actuation assembly 400. Actuation assembly 400 may be used to move a plunger or other body 450, which may have any of the features of plunger 150, 250, 350, proximally or distally within lumen 114 of metering assembly 100, as shown in FIGS. 2A-2C.

Actuation assembly 400 may include an arm 402. Arm 402 may have a finger 404 projecting substantially perpendicularly from a longitudinal axis of arm 402. Finger 404 may be configured to engage with a surface of plunger 450. For example, plunger 450 may include a flange 444 on a proximalmost end of plunger 444. Finger 404 may be positioned distally of flange 444, so that when arm 402 moves proximally, it engages with and exerts a force on flange 444, pulling plunger 450 proximally. Arm 402 may be attached to an actuation mechanism, such as actuation mechanism 30, which may include a trigger, lever, or other structure. When actuation mechanism 30 is activated, arm 402 may move in the second direction, via, e.g., the trigger or lever.

Actuation assembly 400 may also include a guide 410. Guide 410 may be an elongated member extending along a longitudinal axis, or may be a surface of body 112. Guide 410 may extend generally parallel to arm 402. Guide 410 may include a protrusion 412, which may extend toward arm 402. Protrusion 412 may have rounded surfaces, as shown in FIGS. 5A-5B or may have an alternative shape. A shape of protrusion 412 may be chosen to interact with finger 404, as described below.

A spring 460 may be fixed to a portion of arm 402, such as a portion of arm 402 near finger 404. As discussed in further detail below, spring 460 may be configured to deliver a force in a direction that is transverse to a longitudinal axis of plunger 450 and/or guide 410. A spring 420 may be fixed to a proximal end of plunger 450 and may have any of the qualities of springs 220, 320, described above.

In operation, before a user activates actuation mechanism 30, actuation assembly 400 may be in the first configuration of FIG. 5A, which may correspond to the configuration of FIG. 2B. Springs 420, 460, may be in relaxed states, at their natural lengths.

A user may activate actuation mechanism 30, causing arm 402 to move in the second direction (proximally), as described above. Fluid may begin flowing through fluid inlet 120, or a flow of fluid may be delayed until a time described below. As arm 402 moves in the second direction, finger 404 may contact flange 444 (or another portion of plunger 450), exerting a force on plunger 450 in the second direction. Plunger 450 may move in the second direction, along with arm 402. As plunger 450 moves in the first direction, plunger 450 may compress spring 420. Movement of arm 402 may also compress spring 460, if spring 460 is aligned such that a component of spring 460 extends parallel to arm 402, as shown in the Figures. Initially, guide 410, including protrusion 412, may not interfere with movement of arm 402. As plunger 450 moves proximally past agent inlet 118, agent 16 may begin to flow through agent inlet 118.

When finger 404 encounters protrusion 412 of guide 410, protrusion 412 may exert a force on finger 404 that causes finger 404 to move in a direction that is transverse to a longitudinal axis of plunger 450 (a direction that is at least partially downward in the figures). As shown in FIG. 5B, this movement of finger 404 may cause finger 404 to disengage with flange 444 (or another portion of plunger 450). Because finger 404 is no longer in contact with plunger 450, it may no longer exert a force on plunger 450. When finger 404 disengages with plunger 450, a position of plunger 450 may correspond to the position of plunger 150 in FIG. 2C.

A restoring force of spring 420 may cause plunger 450 to move in the first (distal) direction (to the left in the Figures). Plunger 450 may contact agent 16 that has passed through agent inlet 18, pushing agent 16 distally toward fluid inlet 120 until spring 420 is at its natural length again (e.g., when a position of plunger 450 corresponds to a position of plunger 150 in FIG. 2B). Fluid may begin flowing through fluid inlet 120 at approximately this time, so that agent 16 may combine with fluid from fluid inlet 120 and may pass through outlet 134. Actuation mechanism 30 may be released, and a flow of fluid via fluid inlet 120 may cease. Spring 460 may exert a restoring force on arm 402 so that finger 404 may reengage with plunger 450 (e.g., flange 444) after arm 402 is returned to the position shown in FIG. 5A. Alternatively, arm 402 may be formed of flexible, resilient material or shape memory material (e.g., long, flexible material) biased into the configuration shown in FIG. 5A.

Figure 6A:
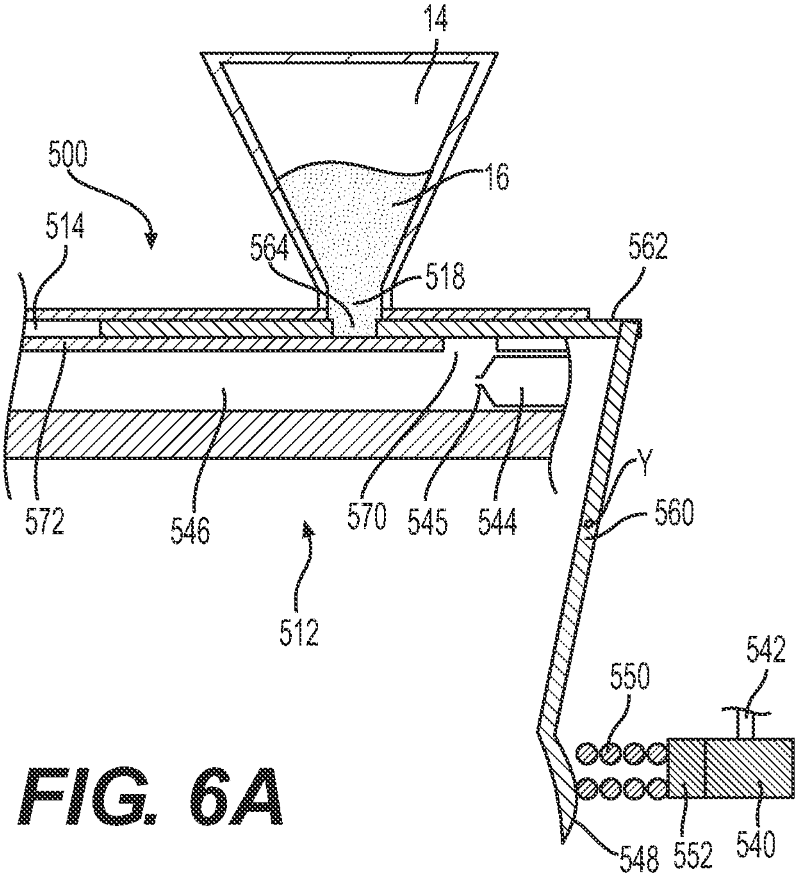
Figure 6B:
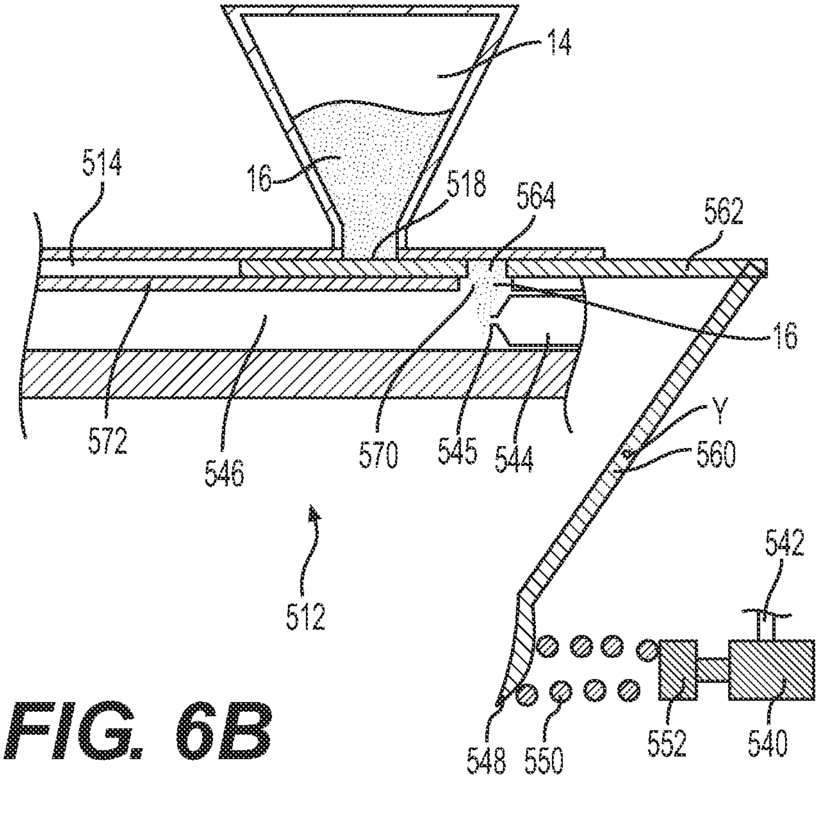

FIGS. 6A-6B show another exemplary metering assembly 500 for use in agent delivery system 10. Metering assembly 500 may include a body 512, which may have any of the properties of bodies 12, 112, above. Body 512 may be configured to receive enclosure 14 (or other source) storing an agent 16. Body 512 may include threads, grooves, ridges, or other features for mating with corresponding features of enclosure 14.

A first lumen or chamber 546 may be formed in body 512. First lumen 546 may be in fluid communication with an outlet, such as outlet 34. A nozzle 544 may include an opening 545. An interior chamber of nozzle 544 may be in fluid communication with first lumen 546 via opening 545. Nozzle 544 may be disposed within first lumen 546 or may otherwise be in communication with first lumen 546. Nozzle 544 may receive fluid from an inlet (e.g., fluid inlet 120). A flow of fluid into nozzle 544 may be controlled by a valve 540, such as a button valve, which may control passage of fluid into passage 542 which is in fluid communication with nozzle 544. Valve 540 may be opened by depressing a trigger 548. Trigger 548 may compress a spring 550, which may exert a force on a button 552, which may open valve 540.

Trigger 548 may also be connected to an arm 560, which may be pivotable about a point Y. Arm 560 may be connected to a slider, piston, plunger, or other body 562, via a hinge or similar structure. An opening 564 may be formed in slider 562. Slider 562 may be slidably received within a second lumen or chamber 514 of body 512. Second lumen 514 may have a longitudinal axis that extends parallel or approximately parallel to a longitudinal axis of first lumen or chamber 546. Second lumen 514 may be in fluid communication with enclosure 14, via an agent inlet 518. A wall 572 may separate first lumen 546 from second lumen 514. An opening 570 may be formed in wall 572, placing first lumen 546 in fluid communication with second lumen 514. Opening 570 may be longitudinally aligned with or approximately aligned with opening 545 of nozzle 544. Opening 570 may be proximal to agent inlet 518.

When trigger 548 is depressed or released, arm 560 may rotate about point Y. Slider 562 may, via its pivoting connection with arm 560, move in the second direction (proximally) or in the first direction (distally). In some configurations (FIG. 6A), opening 564 may be in fluid communication with an agent inlet 518. In other configurations (FIG. 6B), opening 564 may be in fluid communication with opening 570.

FIG. 6A shows metering assembly 500 in a first configuration. In the first configuration, opening 564 in of slider 562 may be aligned with or otherwise in fluid communication with agent inlet 518, such that agent 16 may flow into opening 564. Slider 562 may be sized such that slider 562 has substantially the same cross-sectional width as second lumen 514. Additionally or alternatively, slider 562 or second lumen 514 may include seals disposed thereupon. Therefore, agent 16 may not move within second lumen 514, along the sides of slider 562. Agent 16 may therefore be captured within opening 564. In the first configuration, trigger 548 may be depressed.

Delivery system 10 may optionally be shipped with metering assembly 500 in the first configuration, with trigger 548 depressed via a collar or other mechanism, compressing spring 550. Thus, delivery system 10 may optionally be shipped with a dose of agent 16 disposed within opening 564. Prior to use (e.g., prior to connection with a source of pressurized fluid), a user may remove the collar, which may result in spring 550 returning to a natural length, returning trigger 548 to an undepressed state, and transitioning metering assembly 500 to the second configuration of FIG. 6B. Opening 564 may move proximally from fluid inlet 518 to opening 570 of wall 572, along with the agent 16 received within opening 564. Opening 564 may thus shuttle agent 16 from fluid inlet 518 to opening 570. In the second configuration of FIG. 6B, opening 564 may be aligned with or otherwise in fluid communication with opening 570 of wall 572. In the second configuration, the dose of agent 16 may pass from opening 564 into opening 570, and into first lumen 546, near opening 545 of nozzle 544.

In both the first configuration and the second configuration, enclosure 14 may not be in fluid communication with nozzle 544 (which is a source of fluid). Agent 16 may be shuttled via opening 564, but opening 564 and other components of metering assembly 500 may be configured so that enclosure 14 is never in fluid communication with a source of fluid (e.g., nozzle 544).

Alternatively, delivery system 10 may be shipped in the second configuration, with trigger 548 undepressed, and no agent may be received within opening 564. A user may depress trigger 548 so as to initially place metering assembly 500 in the first configuration to cause a dose of agent 16 to enter opening 564, as described above. For example, the user may transition metering assembly 500 to the first configuration prior to connecting delivery system 10 to a source of fluid, so that fluid is prevented from flowing when trigger 548 is depressed. Alternatively, if the fluid source is connected to delivery system 10 prior to the first transition of metering assembly 500 to the first configuration, a flow of fluid without agent 16 may pass through outlet 34 when metering assembly 500 is transitioned to the first configuration (depressing of trigger 548 causes opening of valve 540, as discussed above). Trigger 548 may then be released to transition metering assembly 500 to the second configuration and to shuttle a dose of agent 16 into first lumen 546, as described above.

As a further alternative, a valve (not shown) may be present in lumen 546 (e.g., near outlet 34). The valve may prevent flow of agent 16 past the valve. During manufacture, trigger 548 may be depressed once and then released (transitioning metering assembly 500 to the first configuration and then back to the second configuration), causing a dose of agent 16 to be present in lumen 546. The dose of agent 16 may be prevented from exiting outlet 34 until depressing of trigger 548 by a user causes a flow of fluid, as described in further detail below. A flow of fluid may cause the valve to open.

Once a dose of agent 16 is deposited within lumen 546, as a result of the actions described above, a user may depress trigger 548 while delivery system 10 is connected to a source of fluid, placing metering assembly 500 into the first configuration (FIG. 6A). Depressing trigger 548 may cause valve 540 to open, as described above. Fluid may pass through nozzle 544 and out of opening 545, into lumen 546, where the fluid may combine with the dose of agent 16. The combined fluid and agent 16 may then pass through outlet 34 to be delivered to a treatment site (via, e.g., catheter 36). At the same time, another dose of agent 16 may enter opening 564, as described above. When trigger 548 is released (and metering assembly 500 is transitioned to the second configuration of FIG. 6B), that dose of agent 16 may enter lumen 546, so that, when trigger 548 is again depressed, the next dose of agent 16 will be delivered, as described above.

In FIGS. 6A and 6B, agent inlet 518 is distal to opening 570. In an alternative configuration (not shown), opening 570 may be distal to agent inlet 518. In such a configuration, when trigger 548 is not depressed, opening 564 may be in fluid communication with agent inlet 518, allowing a dose of agent 16 to enter opening 564. When trigger 548 is pressed, opening 564 may slide in the first direction (distally) so that opening 564 is in fluid communication with opening 570, delivering the dose of agent 16 to first lumen 546. Opening of valve 540 upon depression of trigger 548 may be timed so that fluid will begin to flow once the dose of agent 16 has been delivered into first lumen 546, or flow of fluid may begin before or during delivery of the dose of agent 16 into first lumen 546 (sealing of portions of metering assembly 500 may prevent fluid from flowing through second lumen 572).

Figure 7A:
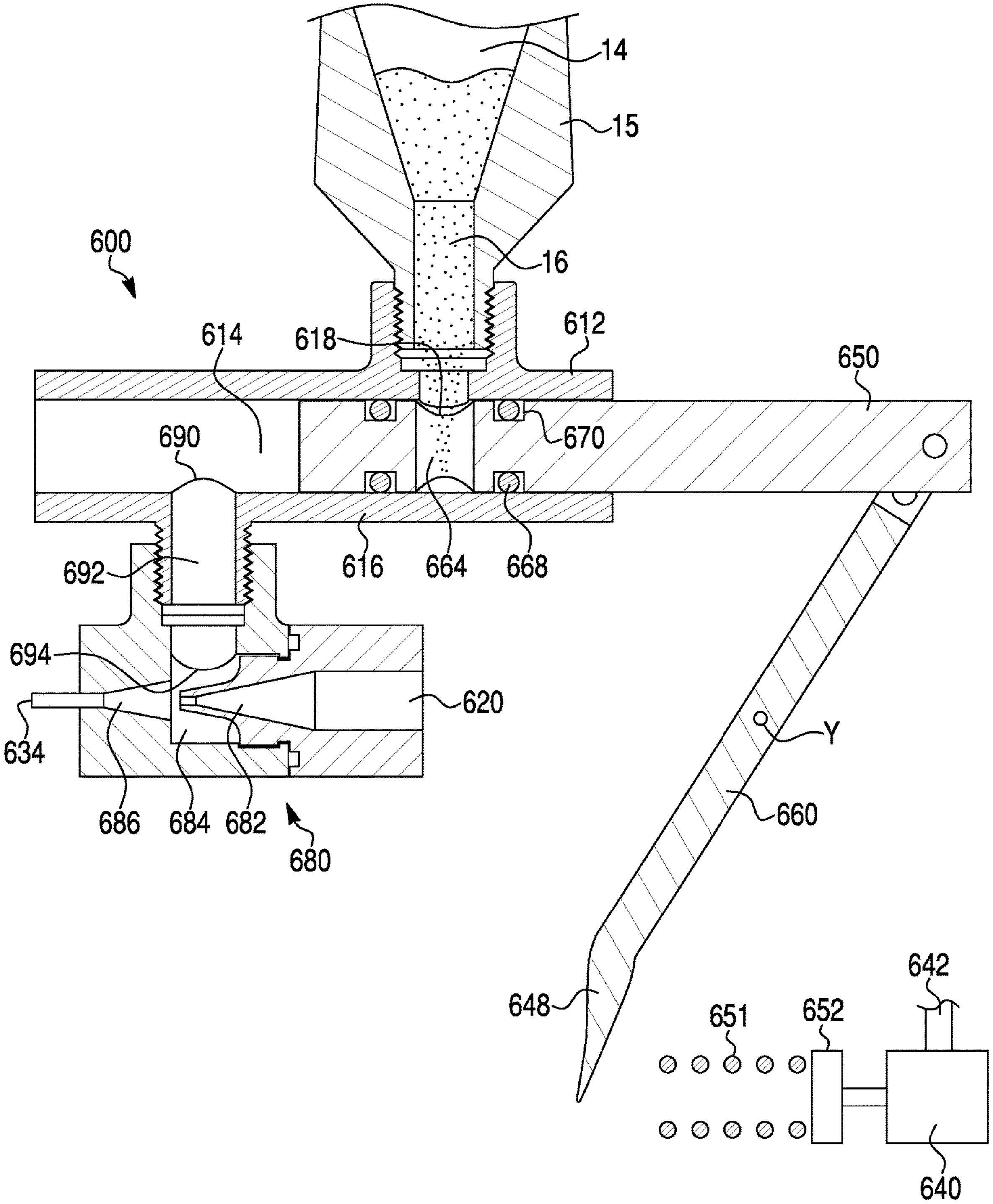
Figure 7B:
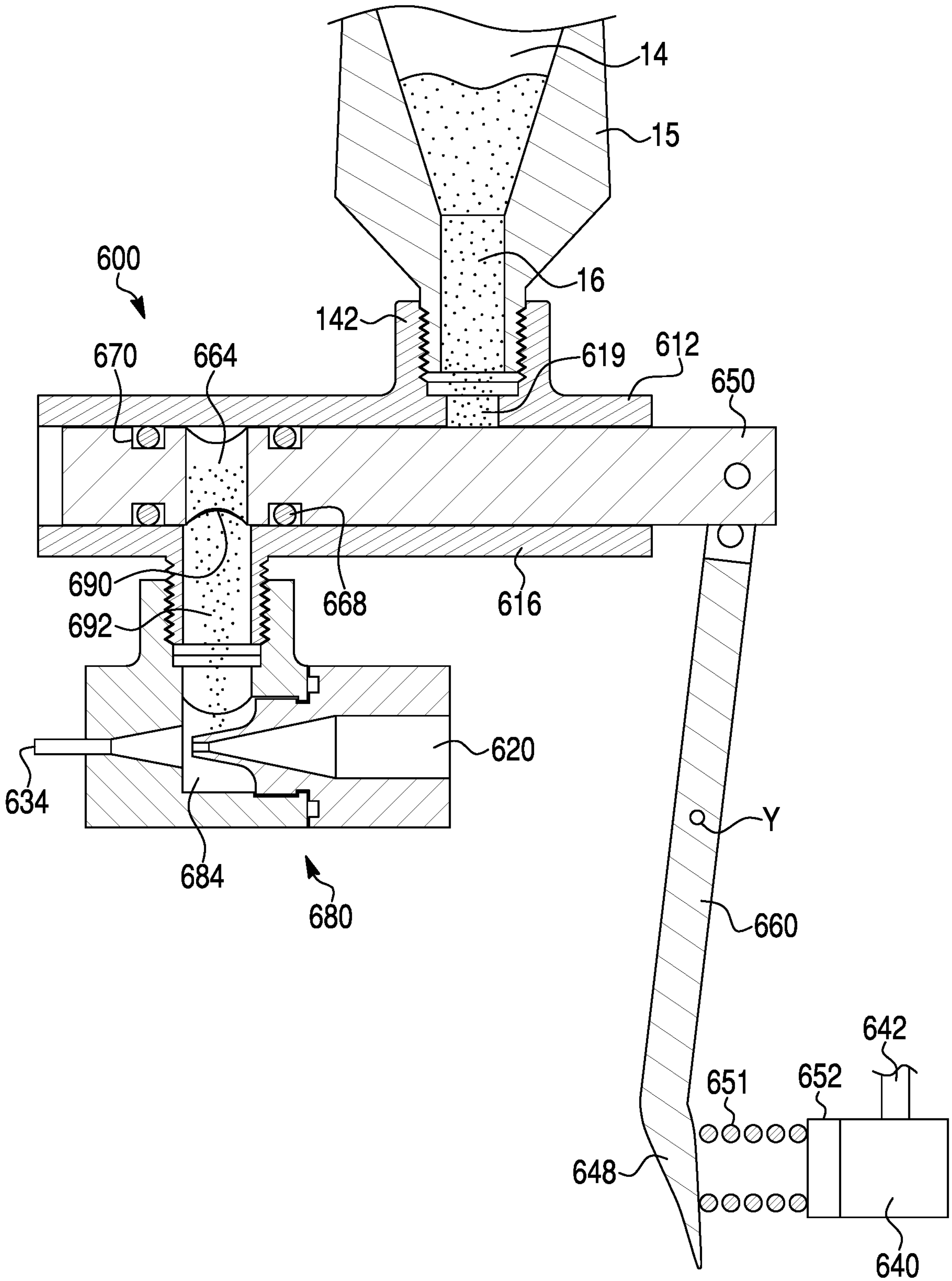

FIGS. 7A and 7B show another example metering assembly 600. Metering assembly 600 may have any of the qualities of metering assemblies 100, 500, described above. Metering assembly 600 may include a plunger 650, which may have qualities of plunger 150, described above. Plunger 650 may be actuated by an arm 660 having a trigger 648, which may have any of the properties of arm 560 and trigger 548, respectively. Alternatively, actuation assemblies 200, 300, 400 may be used in conjunction with plunger 650.

Metering assembly 600 may include a body 612, which may have any of the properties of bodies 12, 112, 512, above. Body 612 may be configured to receive enclosure 14, by any of the mechanisms described above with respect to bodies 12, 112, 512. A first lumen or chamber 614 may be formed in body 612. A longitudinal axis of lumen 614 may extend substantially perpendicularly to a longitudinal axis of enclosure 14.

A plunger 650 may be slidably received within lumen 614. Plunger 50 may include a hole 664 formed therein. A longitudinal axis of hole 664 may extend substantially parallel to a longitudinal axis of enclosure 14, and substantially perpendicularly to a longitudinal axis of lumen 614. Hole 664 may extend through an entirety of plunger 650, substantially perpendicularly to a longitudinal axis of plunger 650. Seals 668 may be disposed about an outer perimeter of plunger 650. Each seal 668 may be fitted, for example, about a groove 670 formed on an outer surface of plunger 650. Seals 668 may have properties (e.g., material and dimensions) such that plunger 650 is slidable within lumen 614 but fluids, agent 16, or other materials may not pass between seals 668 and a surface that defines lumen 614.

Plunger 650 may be moved from a first configuration (see FIG. 7A) to a second configuration (see FIG. 7B) via trigger 648 and arm 660. Arm 660 may be rotatable about an axis Y, similarly to arm 560. Arm 660 may be pivotably connected to plunger 650, via, e.g., a hinge. For example, openings in arm 660 and plunger 650 may couple arm 660 to plunger 650. As arm 660 rotates about axis Y, plunger 650 may be moved along a longitudinal axis of lumen 614/plunger 650. Plunger 650 may be prevented from moving in other directions (e.g., radial directions) by walls that define lumen 614.

Trigger 648 may be operative to control a flow of fluid, as described in further detail below. For example, a valve 640 may have any of the properties of valve 540. Valve 640 may be opened by depressing trigger 648. Trigger 648 may compress a spring 651, which may exert a force on a button 652, which may open valve 640.

Metering assembly 600 may also include a mixing assembly 680 to facilitate mixing of agent 16 with fluid. Mixing assembly 600 may include a first nozzle 682 which receives fluid from a fluid inlet 620. Fluid inlet 620 may be in fluid communication with a passage 642 extending from valve 640. Valve 640 may control fluid flow through fluid inlet 620. Fluid may pass from fluid inlet 620, into nozzle 682, and into a mixing chamber 684. Mixing chamber 684 may be in fluid communication with lumen 614 via a passage 692, depending upon a position of plunger 650, as discussed below. As discussed in further detail below, fluid from fluid inlet 620 and agent 16 may combine together in mixing chamber 684. The combined fluid and agent 16 may pass through a second nozzle 686 in order exit at outlet 634.

In operation, when trigger 648 is not depressed by an operator, plunger 650 may be in the position shown in FIG. 7A. Opening 664 may be aligned with and in fluid communication with agent inlet 618 and enclosure 14. Agent 16 may flow through agent inlet 618 and into opening 664, where it may be captured. In the configuration where trigger 648 is not depressed, mixing assembly 680, including fluid inlet 620, may not be in fluid communication with agent inlet 618 (or enclosure 614). Seals 668 may cause or contribute to the lack of fluid communication.

Depressing trigger 648 may cause fluid to flow through valve 640, and through fluid inlet 620. Depressing trigger 648 may also cause plunger 650 to transition to the configuration shown in FIG. 7B by moving distally (to the left in FIGS. 7A-7B). As plunger 650 moves distally, agent 16 which had flowed into and was captured by opening 664 may move distally, carried by the distal movement of opening 664. When plunger 650 is in the second configuration of FIG. 7B, opening 664 may be aligned with passage 692, such that opening 664 is in fluid communication with passage 692 and therefore mixing chamber 684. The agent 16 captured by opening 664 may flow from opening 664, through passage 692, and into mixing chamber 684. There, it may combine with fluid from fluid inlet 620. The combined fluid and agent 16 may pass through outlet 634.

As with the first configuration (FIG. 7A), agent inlet 620 is not in fluid communication with enclosure 14 in the second configuration (FIG. 7B). Plunger 650, which includes seals 668, may prevent agent or fluid from flowing between enclosure 14 and fluid inlet 620 in any configuration of metering assembly 600. Although opening 664 may serve to shuttle agent 16 between enclosure 14 and mixing chamber 684, enclosure 14 and mixing chamber 684 may never be in fluid communication.

Components of metering assembly 600, including trigger 648, plunger 650, and valve 640, may be configured so as to appropriately time a release of agent 16 and/or fluid into mixing chamber 684. For example, fluid may flow through fluid inlet 620 before, after, or simultaneously to the initial flow of agent 16 into mixing chamber 684.

In an alternative, when trigger 648 is not depressed, plunger 650 may be in a configuration such that opening 664 is not aligned with and in fluid communication with agent inlet 618. For example, plunger 650 may be displaced to the right of where it is shown in FIG. 7A, such that opening 664 is proximal of agent inlet 618. When the trigger 648 is depressed, opening 664 may move distally (to the left in the Figures), until opening 664 begins to overlap with agent inlet 618, at which time agent 16 may begin to flow into opening 664. Agent 16 may continue to flow into opening 664 until opening 664 no longer overlaps with agent inlet 618 (when an entirety of opening 664 is distal to agent inlet 618). Opening 664 may continue to move distally until opening 664 is aligned with passage 692, as described above. In such an alternative configuration, agent 16 may never be static within opening 664, because opening 664 may be moving distally while powder 16 flows into opening 664.

While principles of the present disclosure are described herein with reference to illustrative examples for particular applications, it should be understood that the disclosure is not limited thereto. Those having ordinary skill in the art and access to the teachings provided herein will recognize additional modifications, applications, and substitution of equivalents all fall within the scope of the examples described herein. Accordingly, the invention is not to be considered as limited by the foregoing description.

We claim:

1. A device for delivering an agent, comprising an outlet;

a fluid inlet for receiving a fluid, and in fluid communication with the outlet;

a chamber for receiving the agent through an agent inlet, and in fluid communication with the outlet; and a body received within the chamber, wherein the body is movable in first and second directions along a longitudinal axis of the chamber;

wherein, in a first configuration of the body, a plurality of particles of the agent flows into the chamber via the agent inlet, wherein, in a second configuration of the body, the agent is prevented from flowing into the chamber via the agent inlet, and wherein, when the body is transitioned from the first configuration to the second configuration, the plurality of particles of the agent is moved from a first position along the longitudinal axis of the chamber to a second position along the longitudinal axis of the chamber; and wherein, when in the first configuration, the body is positioned to obstruct the plurality of particles received in the chamber from moving towards the fluid inlet, when transitioning from the first configuration towards the second configuration the body is positioned relative to the chamber such that only a first amount of the fluid from the fluid inlet is delivered via the outlet prior to delivering the plurality of particles of the agent from the chamber when the body arrives to the second configuration, and when in the second configuration, the body is repositioned to unobstruct the plurality of particles from moving towards the fluid inlet via gravity such that a mixture of a second amount of the fluid from the fluid inlet and the plurality of particles of the agent from the chamber is generated inside the device after delivering the first amount of the fluid and prior to the mixture exiting the outlet.

2. The device of claim 1, wherein, when the body is in the second configuration, the second amount of the fluid flows into the outlet via the fluid inlet in combination with the plurality of particles of the agent.

3. The device of claim 2, wherein the fluid inlet is located between (a) the outlet for delivering the second amount of the fluid combined with the plurality of particles of the agent from the chamber and (b) the agent inlet.

4. The device of claim 1, further comprising an actuator coupled to the body, wherein the body transitions from the first configuration to the second configuration due to a force applied to the body in response to actuation of the actuator.

5. The device of claim 1, further comprising a source of the agent, wherein the source is coupled to the chamber.

6. The device of claim 1, wherein the chamber is a first chamber, further comprising a second chamber, wherein the body defines a body opening, wherein, in the first configuration, the body opening is in fluid communication with the agent inlet, and wherein, in the second configuration, the body opening is in not in fluid communication with the agent inlet and is in fluid communication with a chamber opening between the first chamber and the second chamber.

7. The device of claim 6, wherein the body is connected to an arm via a hinge.

8. The device of claim 7, wherein the arm is connected to a trigger, wherein depressing the trigger causes the arm to pivot and causes the body to move in the first direction.

9. The device of claim 1, wherein the device is configured to deliver:

the mixture of the second amount of the fluid and the plurality of particles of the agent when the body is in the second configuration.

10. The device of claim 1, further comprising an actuator that is configured to transition the body to each of the first configuration and the second configuration upon a single actuation.

11. The device of claim 10, wherein, in response to the single actuation, the actuator is configured to release (1) the first amount of the fluid when transitioning the body from the first configuration towards the second configuration and (2) the mixture when the body is in the second configuration.

12. The device of claim 11, wherein, in response to ceasing the single actuation, the actuator is configured to transition the body from the second configuration to a final configuration and terminate release of the mixture through the outlet.

13. The device of claim 12, wherein in the final configuration, the body is not positioned in the first configuration, is incapable of delivering any fluid from the device, and blocks the plurality of particles of the agent from flowing into the chamber via the agent inlet.

14. A device for delivering an agent, comprising an outlet;

a fluid inlet in fluid communication with the outlet;

a chamber in fluid communication with the agent in a first configuration and the outlet in a second configuration; and a body that is configured to move relative to the chamber between the first configuration and the second configuration;

wherein, in the first configuration, the body is positioned relative to the chamber such that the body is configured to receive the agent, and in the second configuration, the body is positioned relative to the chamber such that the body is configured to release the agent;

wherein the body is positioned relative to the chamber to obstruct the agent stored in the chamber from moving towards the fluid inlet when in the first configuration, and the body is positioned such that only a first amount of a fluid from the fluid inlet without the agent is delivered via the outlet when the body is moved from the first configuration towards the second configuration, and the body is repositioned relative to the chamber to unobstruct the agent from moving towards the fluid inlet via gravity such that a mixture of a second amount of the fluid from the fluid inlet with the agent from the chamber is generated inside the device when the body is in the second configuration and prior to the mixture exiting the outlet.

15. The device of claim 14, wherein the body includes a channel having a longitudinal length that extends through an entirety of the body, and the channel is configured to receive the agent when the body is in the first configuration and release the agent when the body is in the second configuration.

16. A device for delivering an agent, comprising:

an outlet;

a fluid inlet in fluid communication with the outlet; and a body that is movable relative to a chamber for selectively receiving the agent;

wherein the body is configured to be transitioned from a first configuration towards a second configuration, such that:

in the first configuration the body is positioned relative to the chamber to block the agent from exiting the chamber and moving towards the fluid inlet;

when transitioning from the first configuration towards the second configuration the body is positioned such that only a first amount of a fluid from the fluid inlet is deliverable to the outlet without the agent; and upon arriving to the second configuration the body is repositioned relative to the chamber to release the agent received within the chamber towards the fluid inlet via gravity, such that a mixture of a second amount of the fluid from the fluid inlet and the agent from the chamber is created inside the device after delivering the first amount of the fluid to the outlet and prior to the mixture exiting the outlet.

17. The device of claim 16, further comprising an actuator that is configured to transition the body between the first configuration, the second configuration, and a final configuration;

wherein, upon an actuation, the actuator is configured to release the first amount of the fluid without the agent and position the body relative to the chamber to receive the agent when transitioning the body to the first configuration.

18. The device of claim 17, wherein, upon the actuation, the actuator is configured to position the body relative to the chamber to release the mixture of the second amount of the fluid with the agent when the body is in the second configuration.

19. The device of claim 18, wherein, upon ceasing the actuation, the actuator is configured to terminate release of the mixture of the second amount of the fluid with the agent and position the body relative to the chamber to block receipt of the agent within the body when transitioning the body from the second configuration to the final configuration.

20. The device of claim 19, wherein in the final configuration, the body is not positioned in the first configuration or the second configuration, is incapable of delivering any fluid from the device, and blocks additional agent from flowing into the chamber.

* * * * *